(12) United States Patent
Boelen (10) Patent No.: US 11,291,353 B2
(45) Date of Patent: Apr. 5, 2022

(54) MINIATURE LENS-FIBER CONNECTOR WITH LIVE FOCUSING CAPABILITY

(71) Applicant: Neurescence Inc., Toronto (CA)

(72) Inventor: Sander Johannes Boelen, Vaudreuil-Dorion (CA)

( * ) Notice: Subject to any disclaimer, the term of this patent is extended or adjusted under 35 U.S.C. 154(b) by 351 days.

(21) Appl. No.: 16/627,629

(22) PCT Filed: Nov. 9, 2018

(86) PCT No.: PCT/CA2018/051422
§ 371 (c)(1),
(2) Date: Dec. 30, 2019

(87) PCT Pub. No.: WO2019/090432
PCT Pub. Date: May 16, 2019

(65) Prior Publication Data
US 2021/0145260 A1 May 20, 2021

Related U.S. Application Data

(60) Provisional application No. 62/584,118, filed on Nov. 10, 2017.

(51) Int. Cl.
*G02B 6/26* (2006.01)
*G02B 7/02* (2021.01)
(Continued)

(52) U.S. Cl.
CPC ...... *A61B 1/00188* (2013.01); *A61B 1/00126* (2013.01); *G02B 6/262* (2013.01);
(Continued)

(58) Field of Classification Search
None
See application file for complete search history.

(56) References Cited

U.S. PATENT DOCUMENTS 3,941,121 A 3/1976 Olinger et al.
5,359,992 A * 11/1994 Hori ...................... A61B 1/042
403/DIG. 1
(Continued)

FOREIGN PATENT DOCUMENTS

WO 2013007352 A1 1/2013
WO WO-2018184708 A1 * 10/2018 ............... G02B 6/32

*Primary Examiner* — Rhonda S Peace
(74) *Attorney, Agent, or Firm* — Benoit & Côté Inc.

(57) ABSTRACT

An optical imaging connector connects an optical fiber to a lens located adjacent to an imaging target, such as the brain tissue of a laboratory animal. A fiber assembly of the connector includes a ferrule holding the fiber and a ferrule adapter with a radially-extending coupler. The fiber assembly is removably joined to a lens assembly that holds the lens adjacent to a receptacle in which the ferrule is inserted coaxial to the lens. The lens holder has a radially-extending coupler that engages the coupler of the ferrule adapter to hold the two assemblies together. A focus adjustment mechanism, such as a screw, is manually adjustable by a user to change the position of the second coupler relative to the lens holder, and thereby change the axial position of the ferrule in the ferrule receptacle. One or more magnets may be used to provide a mutual attraction between the couplers.

14 Claims, 7 Drawing Sheets

(51) Int. Cl.
*G02B 7/04* (2021.01)
*A61B 1/00* (2006.01)
(52) U.S. Cl.
CPC .............. *G02B 7/022* (2013.01); *G02B 7/04* (2013.01); *A61B 2503/40* (2013.01)

(56) References Cited

U.S. PATENT DOCUMENTS

| | | | |
|---|---|---|---|
| 5,575,757 A | 11/1996 | Kennedy | |
| 5,659,645 A * | 8/1997 | Satake | G02B 6/32 385/33 |
| 5,836,867 A * | 11/1998 | Speier | G02B 23/2484 403/DIG. 1 |
| 6,616,602 B1 * | 9/2003 | Witte | G02B 23/2476 600/173 |
| 6,632,173 B1 * | 10/2003 | Kehr | A61B 1/00188 600/168 |
| 8,343,042 B2 * | 1/2013 | Leiner | A61B 1/00126 600/173 |
| 2007/0206904 A1 | 9/2007 | Sezerman et al. | |
| 2017/0254964 A1 | 9/2017 | Yajima | |
| 2021/0145260 A1 * | 5/2021 | Boelen | G02B 7/022 |

\* cited by examiner

MINIATURE LENS-FIBER CONNECTOR WITH LIVE FOCUSING CAPABILITY

BACKGROUND OF THE INVENTION

Field of the Invention

This invention relates generally to the field of optical connectors and, more specifically, to connectors that couple a lens to an optical fiber.

Description of the Related Art

In many applications, one requires imaging hard to reach places. For accessibility, optical fibers are often used to reach the imaging area. At the end of the fiber, at the imaging site, it is necessary to have a lens to form an image on the end of the fiber that may then be transmitted to the rest of the imaging system.

An example of such an application is the imaging of tissue in the brain of a live, freely moving mammal. In this example, the lens is located in the brain tissue, and an imaging optical fiber must be coupled to the lens to allow the transfer of a focused image away from the imaging site to where the rest of the imaging system resides. In such experiments, it may be necessary to image the brain many times over an extended time period. However, the process of connecting the fiber to the lens, performing the imaging session and disconnecting the fiber from the lens can be clumsy and time-consuming.

In many existing fiber-lens connectors, there are various problems that limit the functionality of the connector. It is often difficult to maintain the focusing properties of the imaging device, as the focus may change from one imaging session to another. It is also frequently difficult to manipulate the connector relative to brain tissue which can sometimes lead to the tissue being damaged. The size and weight of conventional connectors can also be a problem, particularly when trying to image a small mammal, such a mouse and, if they are too big, they can interfere with natural animal movement and behavior. In addition, the coupling of existing connectors is not always completely stable or easily manipulatable by a user.

SUMMARY OF THE INVENTION

In accordance with the present invention, an optical imaging connector is provided that has a fiber assembly that is removably attachable to a lens assembly. The lens assembly has a lens, such as a graded refractive index (GRIN) lens, that may be fixed in position adjacent to an imaging target, such as the brain tissue of a laboratory animal. The fiber assembly may be easily connected and disconnected from the lens assembly such that, when the two assemblies are connected, an image collected by the lens is coupled into an optical fiber of the fiber assembly. Quick detachment and reattachment of the fiber assembly from the lens assembly allows for repeated measurements to be easily taken from an imaging target.

The fiber assembly has an optical fiber ferrule in which is located an optical fiber for transporting an optical image. A ferrule adapter is fixed to the ferrule and has a radial extension with a first coupling portion. The lens assembly has a lens with a distal end configured to be fixed adjacent to an imaging target. The lens is mounted in a lens holder with its proximal end adjacent to a ferrule receptacle of the lens holder that receives the ferrule and maintains it in a substantially co-axial relationship with the lens. The lens holder also has a radial extension with a second coupling portion that engages with the first coupling portion of the ferrule adapter to removably couple the fiber assembly to the lens assembly. In an exemplary embodiment, the first and second coupling portions comprise at least one magnetic element that provides a magnetic attraction between the first and second coupling portions.

The connector also has a focus adjustment mechanism that is part of the lens assembly. The mechanism is manually adjustable by a user to change the longitudinal position of the second coupling portion relative to the lens holder. This, in turn, changes an axial position of the ferrule when it is located in the ferrule receptacle, and thereby changes the focusing, as the distance between the lens and the fiber is also changed. In an exemplary embodiment, the radial extension of the lens holder includes a threaded aperture, and the focus adjustment mechanism makes use of a screw that has an external thread that meshes with the internal thread of the threaded aperture. Rotation of the screw changes a longitudinal position of the second coupling portion, thereby axially moving the ferrule adapter and the ferrule relative to the lens holder.

The first coupling portion and the second coupling portion may also be configured to maintain a constant relative angular orientation between them when the two coupling portions are engaged with each other. A top of the screw used to adjust the focus may act as a detent and extend into a space of the first coupling portion in which it prevents relative rotation between the two coupling portions. Maintaining this common angular orientation between the fiber assembly and the lens assembly ensures that the image transported by the fiber will always have the same orientation relative to the imaging target.

In an alternative embodiment, an optical imaging connector has an optical fiber ferrule in which is located an optical fiber, as well as a ferrule adapter fixed to the ferrule that has an external screw thread and an axially-extending detent on a distal side of the adapter. A lens is configured to have its distal end fixed adjacent to an imaging target, while its proximal end is mounted in a lens holder adjacent to a ferrule receptacle that receives the fiber ferrule and maintains it in a substantially coaxial relationship with the lens. The lens holder has an external screw thread and receives the detent when the ferrule adapter and the lens holder are axially adjacent to each other so as to prevent a relative rotation therebetween. The lens holder may have, for example, a slot into which the detent, which may be an axially-extending tab, is inserted.

The connector includes a focus adjustment mechanism with an internal screw thread that engages both the screw thread of the ferrule adapter and the screw thread of the lens holder. The focus adjustment mechanism is manually rotatable by a user to change a relative longitudinal position between the ferrule adapter and the lens holder, thereby changing an axial position of the ferrule in the ferrule receptacle. In particular, the focus adjustment mechanism may include a nut with screw threads having different thread directions, i.e., right-handed and left-handed, at the two openings of the nut. Thus, rotation of the nut causes the ferrule adapter and the lens holder to move either toward or away from each other. When engaged, the focus adjustment mechanism maintains the ferrule adapter and the lens holder in a substantially coaxial position relative to each other, while rotation of the mechanism to an extreme position provides disengagement of the internal screw thread from the screw threads of the ferrule adapter and the lens holder, allowing detachment of the ferrule from the lens holder.

BRIEF DESCRIPTION OF THE DRAWINGS

In order that the subject matter may be readily understood, embodiments are illustrated by way of examples in the accompanying drawings, in which.

DETAILED DESCRIPTION

Figure 1A:
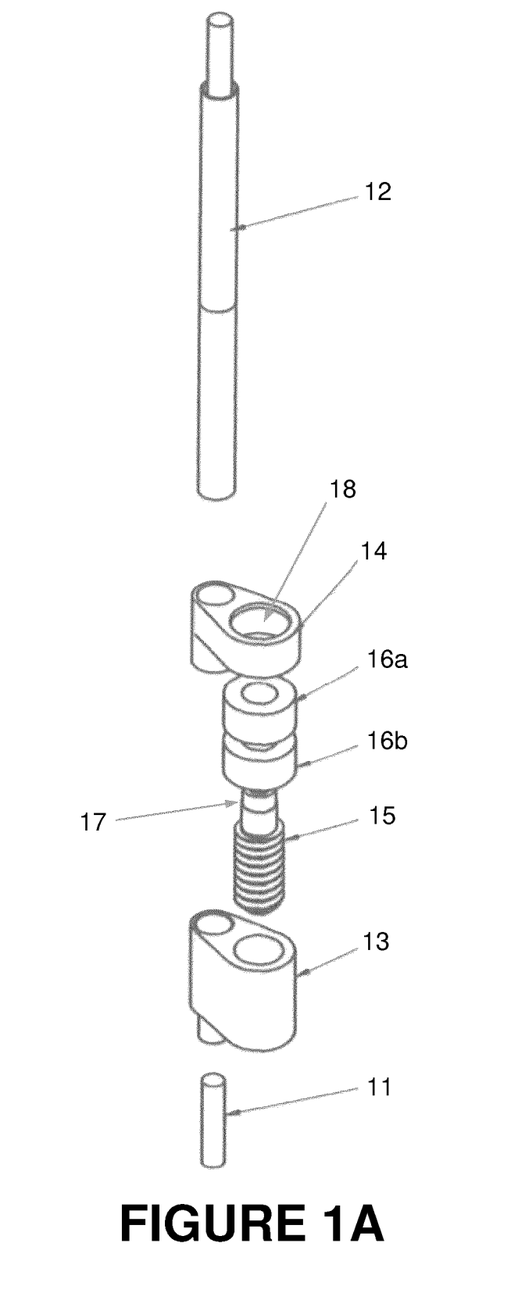
FIG. 1A is an exploded perspective view of a first embodiment of a focus adjustable, stable lens-fiber connector according to the present invention.

Depicted in FIG. 1A is a first embodiment of a lens-fiber connector shown in exploded form. The connector includes two main assemblies, a lens assembly and a fiber assembly, each of which consists of components that are fixed to one another. The two assemblies can, however, be removably coupled together, with the fiber assembly being connected or disconnected from the lens assembly. The fiber assembly includes an optical fiber located in a ferrule 12, to which is attached a ferrule adapter 14. Mounted in the ferrule adapter 14 is a cylindrical magnet 16a, which has a mutual attraction to a cylindrical magnet of the lens assembly, as discussed in more detail below. The lens assembly includes a lens 11 that is located at an imaging site, and resides in a first aperture of a collet 13, the opposite side of which receives the fiber ferrule 12 of the fiber assembly. Also located in the collet 13 is a threaded aperture that receives a focusing screw 15 having threads that mesh with the threads of the collet aperture. Surrounding a portion of the top 17 of the screw 15 is the cylindrical magnet 16b of the lens assembly.

Figure 1B:
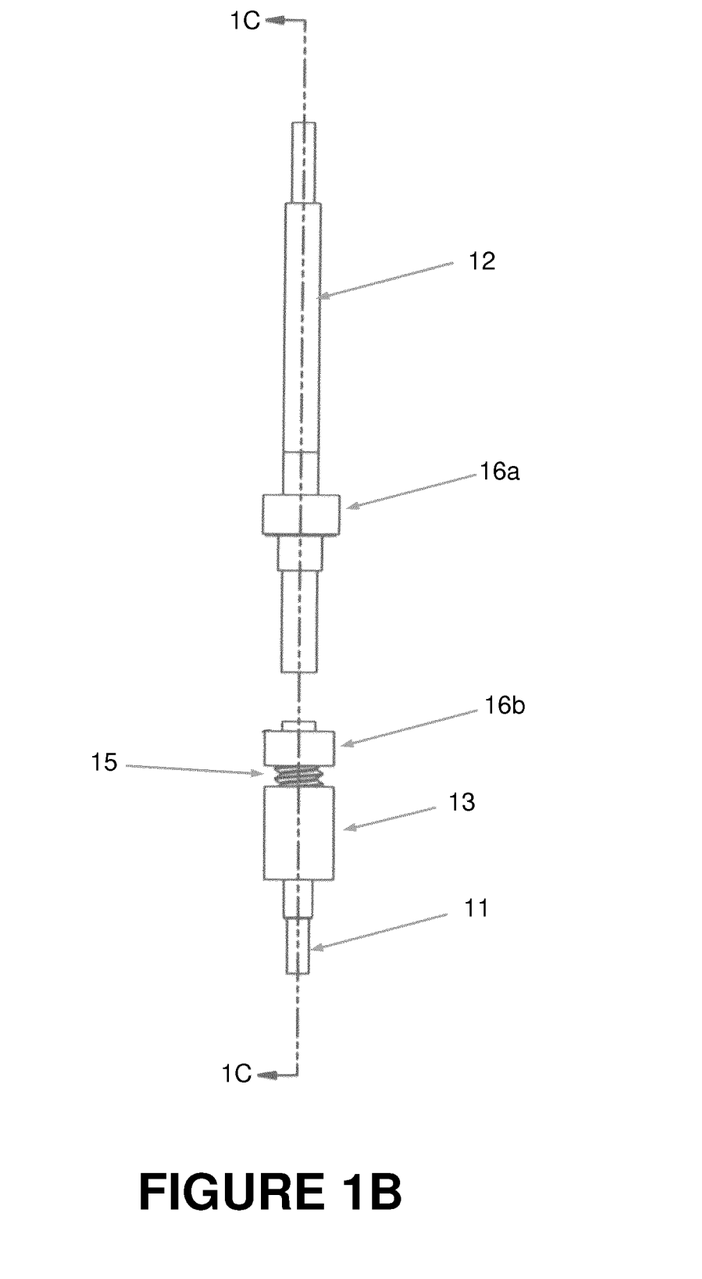
FIG. 1B is a front view of the connector of FIG. 1A.

FIG. 1B is a front view, showing the components of each of the lens assembly and the fiber assembly in an assembled configuration. The two assemblies are shown side-by-side relative to an axis along which they may be connected together during an imaging operation. A section line indicates the perspective of the cross-sectional side view shown in FIG. 1C, which is instructive for an understanding of the system operation.

Figure 1C:
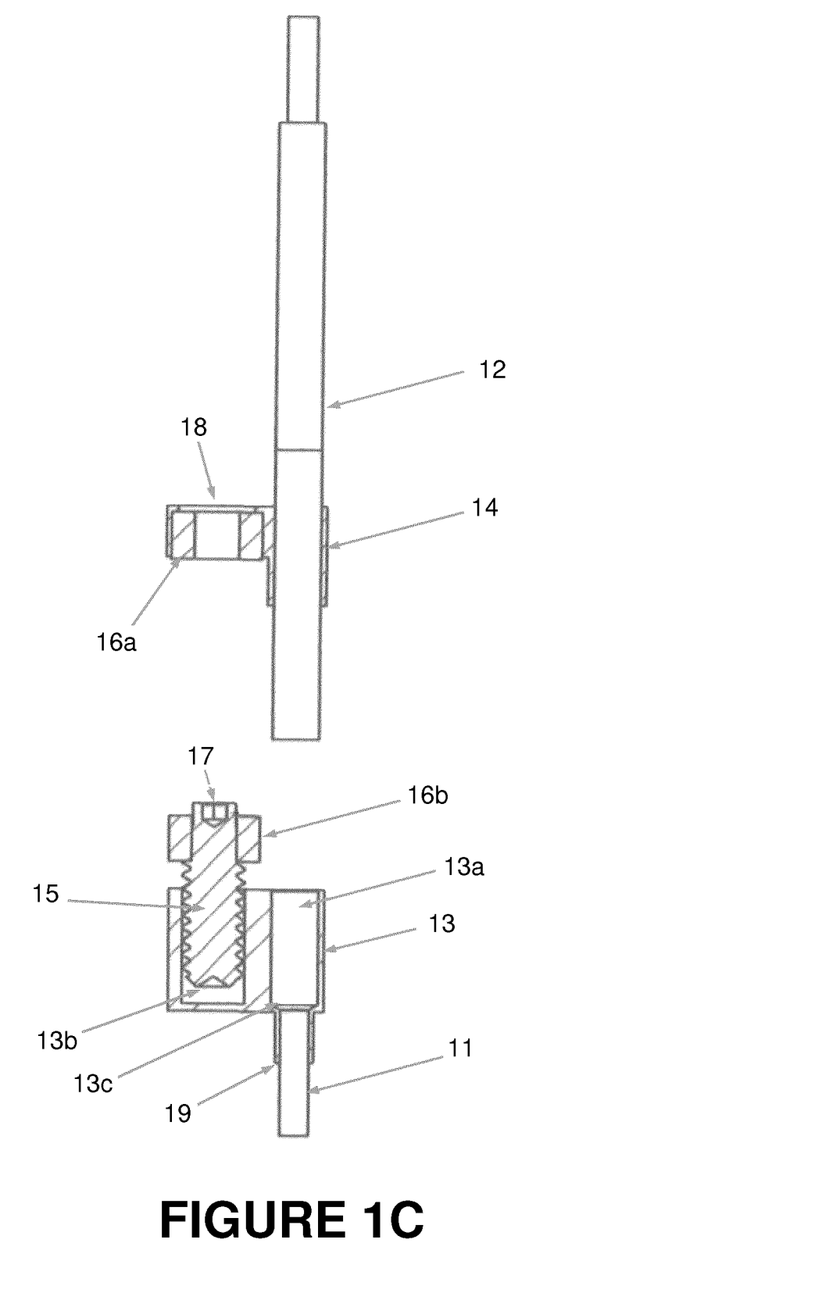
FIG. 1C is a cross-sectional side view of the connector, the direction of the cross section being indicated in FIG. 1B.
Figure 1D:
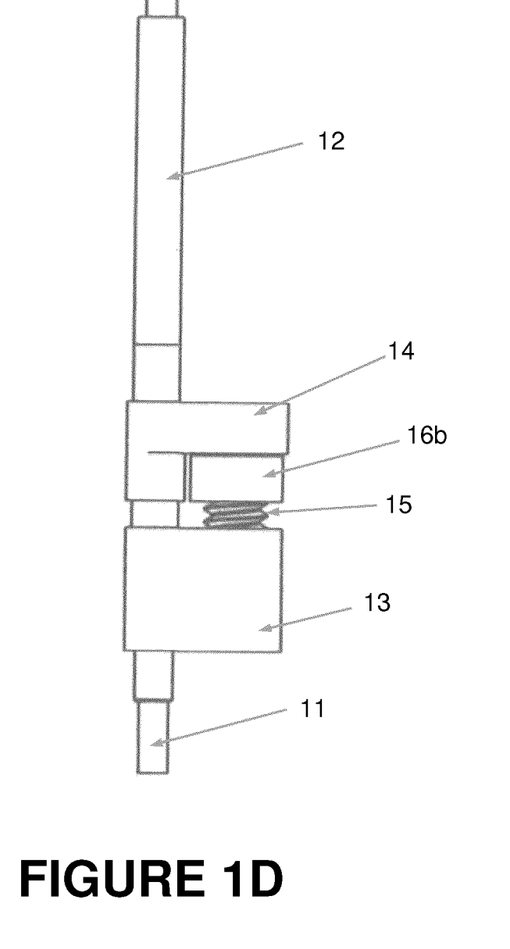
FIG. 1D is a side view of the connector of FIG. 1A showing a side opposite that of FIG. 1C.
Figure 1E:
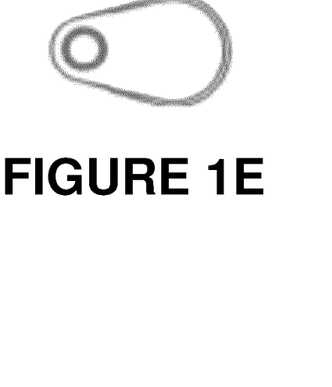
FIG. 1E is a bottom view of the connector of FIG. 1A.

As shown in FIG. 1C, the connector is asymmetrical relative to a longitudinal axis of the connector. The lens 11 is a lens that can have different diameters or lengths and, as mentioned above, in the present embodiment, it is a graded refractive index (GRIN) lens. In this embodiment, the lens has a diameter of 1 mm and a length of about 4 mm, although other sizes are possible. The miniature size of the lens makes it well suited for connection to an anatomical region of interest, such as the brain tissue, of a small mammal, such as a mouse. In a typical imaging situation, the lens is fixed to the brain tissue of the subject using a strong biocompatible glue, such as meta-bond or dental cement. As experiments of this nature require imaging of the brain tissue multiple times over a long period of time (often several months), the lens assembly remains in place during this period, while the fiber assembly is disconnected during periods when imaging is not required.

The lens 11 has a cylindrical exterior and is inserted into a mating cylindrical extension of the collet 13, and is glued to the collet at a precise location within the collet, the glue being applied, for example, at interface 19 shown in FIG. 1C. In the present embodiment, the lens is located in the collet at a position that will provide a minimum distance of about 10 or 20 microns between the proximal end of the lens and the distal end of a fiber of the fiber assembly when the fiber assembly and the lens assembly are connected together. A receiving aperture 13a of the collet 13 into which the fiber is inserted has a tapered surface 13c adjacent to the lens 11 that ensures this minimum distance, and prevents contact between the fiber and the lens, which might otherwise damage the lens or scratch the tip of the fiber.

Another aperture 13b of the collet 13 lies adjacent to the aperture 13a and has an internal screw thread that mates with an exterior thread of screw 15. In this embodiment, longitudinal axes of the apertures 13a and 13b are parallel. As shown in FIG. 1C, the screw 15 has an upper portion that is not threaded and that has a narrower diameter than the threads on the lower portion of the screw. Annular magnet 16b is located around this upper screw portion, the diameter of which is sufficiently small to receive it, while the larger diameter of the screw threads prevents further movement of the magnet down the body of the screw. The height of magnet 16b is such that the top 17 of the screw 15 protrudes out of the magnet by a small amount when the magnet 16b is resting adjacent to the screw threads. This provides access to the screw to allow it to be adjusted by a user either by hand or by an appropriate tool, such as a screwdriver.

Also shown in FIG. 1C are the fiber ferrule 12 and ferrule adapter 14. In this embodiment, the ferrule 12 has a diameter of 1.7 mm and length of approximately 25 mm. As shown in the cross-section of the adapter 14, it is fixed to the exterior of the ferrule 12, and has a laterally-extending magnet holder 18. Located within the magnet holder 18 is cylindrical magnet 16a, which preferably has the same diameter and bore as magnet 16b. Magnet 16a is fixed within the magnet holder 18, which is located to align with the magnet 16b when the fiber assembly and lens assembly are connected together. That is, when the ferrule 12 is inserted in the collet 13, it may be rotated so that the magnets 16a and 16b are adjacent to each other, such that further insertion of the ferrule 12 in the collet results in insertion of the top 17 of screw 15 into the bore of the magnet 16a. The magnets 16a and 16b are mutually attractive, and hold the two assemblies together in this position.

As will be recognized by those skilled in the art, the position of the screw 15 and magnet 16b will affect the relative positioning of the fiber assembly and the lens assembly. The ferrule adapter 14 is fixed to the ferrule 12, such as by gluing, at a position that results in the fiber being adjacent to the tapered surface 13c of the collet 13 when the screw 15 is fully screwed into the threaded aperture of the collet. As the screw 15 is unscrewed from the threaded aperture, the point of contact between the magnets 16a and 16b moves further from collet 13, and the distal end of the ferrule 12 moves away from the tapered surface 13c, while remaining in the receiving aperture 13a. Thus, the distance between the tip of the fiber and the lens, and thereby the focusing of the lens on the fiber, can be changed by adjusting the screw from the top.

When the fiber assembly and lens assembly are connected together, the magnets keep the assemblies, and therefore the fiber and lens, firmly in place. In addition, the location of the top 17 of screw 15 in the bore of the magnet 16a prevents a relative rotational movement between the ferrule 12 and the collet 13, and therefore between the fiber and the lens. This prevents relative rotation of an image from the lens at a detector (not shown) to which the fiber is connected, allowing for easy comparison of images taken at different times.

An opening on the top of the magnet-holding portion 18 of the ferrule adapter 14 provides access to the top of the screw when the fiber assembly and the lens assembly are connected together. Thus, a user can adjust the focus while the fiber and lens are properly positioned relative to each other by turning the screw to change the relative distance between them. In this way, the user can observe the image while changing the fiber-lens distance so as to achieve the best possible focus. Moreover, the frictional resistance of the screw in the threaded aperture of the collet is sufficiently high that there is no slippage of the screw position without it being manually adjusted. Thus, once a desired adjustment is made, the proper focusing position remains for this lens, regardless of how many times the user disconnects and reconnects the fiber assembly. Furthermore, if multiple ferrules with different fibers are used with the system, and all have the same positioning of the fiber relative to the ferrule and the ferrule adapter, the correct focusing position will be maintained for each of the fiber ferrules used with a given lens assembly.

In an embodiment like that of FIGS. 1A-1E, the components of the connector may be assembled in a particular order to ensure a proper optical alignment. First, the screw 15 is located in the threaded aperture of the collet 13 and screwed all the way down. Magnet 16a is glued to the ferrule adapter 14, which is then located on the ferrule, but not yet glued. Magnet 16b is located on the screw head with an orientation that provides mutual attraction between the magnets 16a, 16b, and the GRIN lens 11 is inserted into collet 13. The fiber ferrule is then inserted into the receiving aperture 13a of the collet 13 until it reaches the tapered surface 13c. The fiber ferrule adapter is then positioned on the ferrule 12 so that the magnets 16a, 16b are adjacent to each other. With the connector components in this position, the lens 11 is glued to the collet 13 and the ferrule adapter 14 is glued to the fiber ferrule 12. The magnet 16b is also glued to the top of screw 15. Once the glue sets, the connector components have correct relative positions that allow proper optical alignment that is repeatable when the fiber assembly is disconnected and reconnected to the lens assembly.

The focusing between the lens 11 and the fiber of ferrule 12 is adjustable by rotating the screw to change the distance between a tip of the ferrule 12 and the lens 11. This focusing adjustment allows the connector to compensate for differences in how the lens 11 may be positioned relative to the imaging target, such as the brain tissue of a mammal being examined. Different positioning of the lens may result in different necessary focusing adjustments, but since the grin lens may be fixed in position, and the focusing adjustment remains with the collet 13 and lens 11, the adjustment does not need to be repeated each time the fiber assembly is reconnected to the lens assembly. Moreover, there may be multiple lens assemblies to which one fiber assembly is connected, and since the focusing adjustment for each resides on the lens assembly, there is no need for readjustment once the proper focusing adjustment is made for each lens assembly. Thus, the connector allows for simple, repeatable connections between the fiber assembly and one or more lens assemblies.

The connector provides a number of different advantages, particularly for doing brain imaging of small mammals. As discussed above, the distance between the fiber and the lens 11 remains the same for all imaging sessions, so the user can be confident that the changes they see in the biological tissue result from changes in the tissue, not from the focusing properties of the imaging device. The user can also be confident that the same object plane is being imaged in all imaging sessions, as once the focal distance between lens and fiber is set during the first imaging session, it remains the same for all subsequent imaging sessions. The system also allows the change of focus to be done in a gradual, continuous manner without pushing and pulling on the lens, which prevents injury to brain tissue. Because the same rotational orientation between the fiber assembly and the lens assembly is maintained when the assemblies are disconnected and reconnected, the orientation of the imaging field will also remain the same between different imaging sessions.

The configuration of the connector is also particularly suitable for miniaturized applications like imaging of the brain of a small rodent, such as a mouse. In an exemplary embodiment, the size of the connector is small enough that a number of connectors (e.g., four) can fit on the head of a mouse. For example, in the embodiment shown in FIGS. 1A to 1E, the lens 11 may have a diameter of 1.0 mm, and a length of about 4 mm. With the screw 15 fully inserted into the threaded aperture of the collet 13, the collet has an overall length of about 7.3 mm, and a maximum width of about 5 mm. The ferrule of this embodiment has a diameter of about 1.7 mm and a length of approximately 25 mm. Thus, it can be seen that the connector is particularly suited for miniaturized applications. The weight of the connector is also minimized, e.g., about 300 mg, so that a small rodent can support multiple connectors in a way that the weight does not interfere with natural animal movement and behavior.

The connector is also well suited to use by a single user. In particular, the design allows a user to change the focus when the lens is implanted in the head of an animal, such as a mouse, while the animal is awake and minimally restrained, by allowing, for example, the user to hold the animal with one hand and change the focus with the other hand. A user can do this for a number of implants, e.g. four, very quickly, as the focusing mechanism for each of the lens assembly implants is easily accessible, accurate and fast. Finally, as the subject, e.g. a mouse, moves around with the lens and fiber on its head, the image remains completely stable, as there is no relative movement between the lens and fiber once it is fixed in place.

Shown in FIGS. 2A to 2D is an alternative embodiment of the invention that has a more slender profile than the embodiment of FIGS. 1A-1E. In the exploded perspective view of FIG. 2A, a grin lens 21 is shown adjacent to a collet 23 having an aperture that receives the lens 21. The collet 23 has a slot 26 that receives a key 27 that extends from a fiber ferrule adapter 24 that is fixed on fiber ferrule 22. The collet 23 has a threaded exterior that meshes with an internal thread at a distal end of nut 25, while the ferrule adapter 24 has a threaded exterior that meshes with an internal thread at a proximal end of nut 25.

Figure 2A:
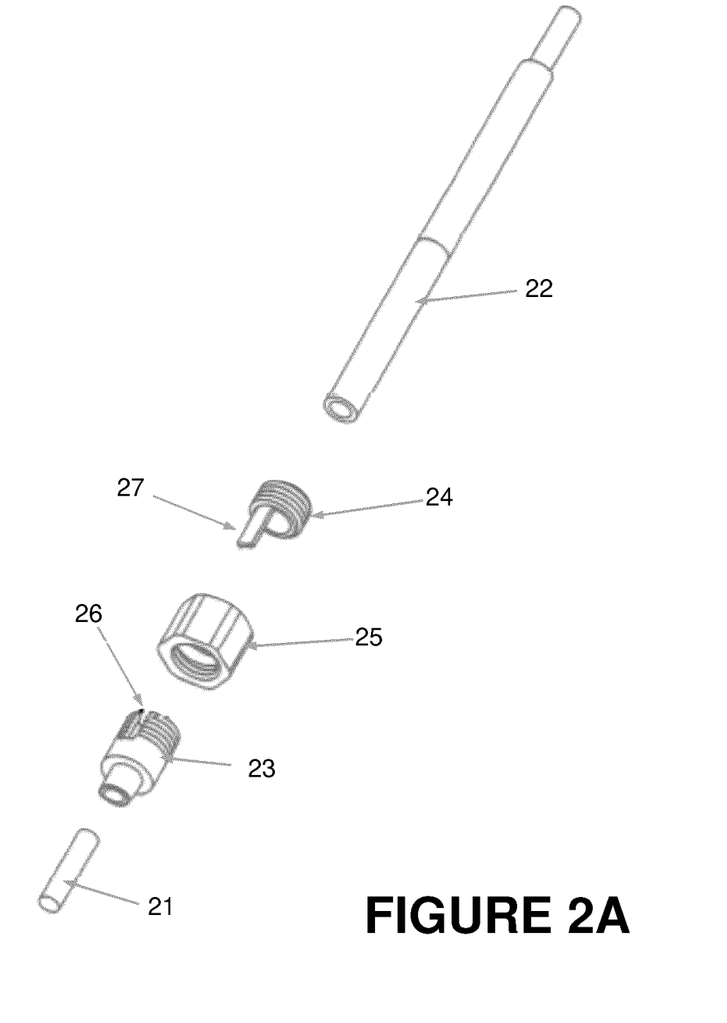
FIG. 2A is an exploded perspective view of a second embodiment of a focus adjustable, stable lens-fiber connector according to the present invention.
Figure 2B:
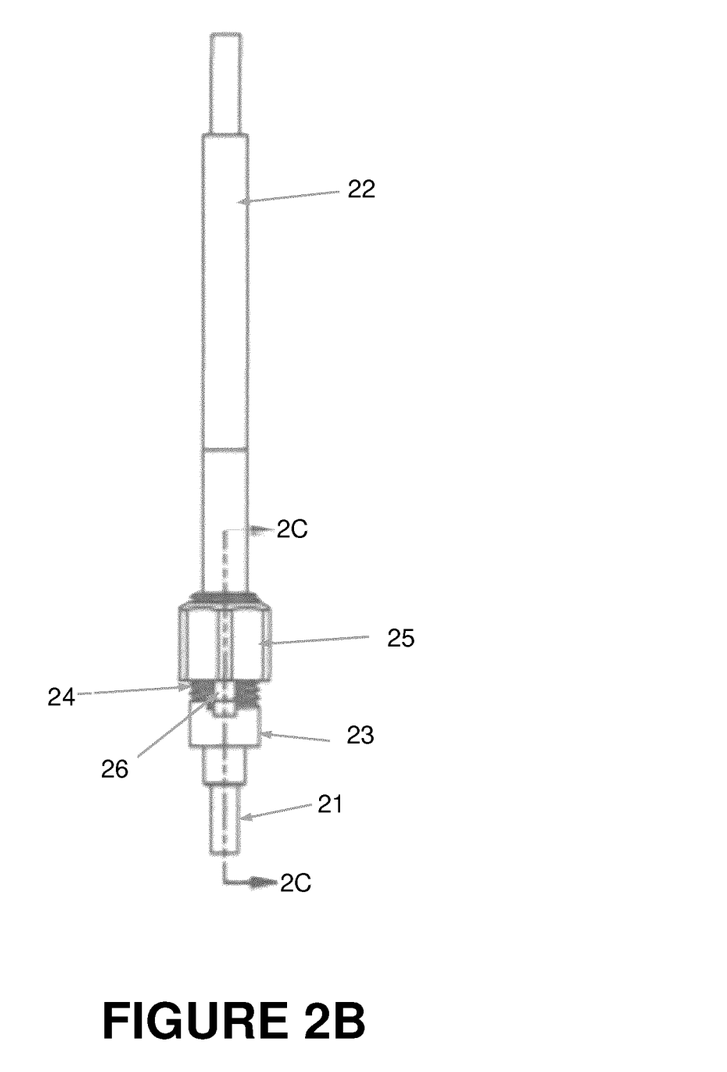
FIG. 2B is a front view of the connector of FIG. 2A.
Figure 2C:
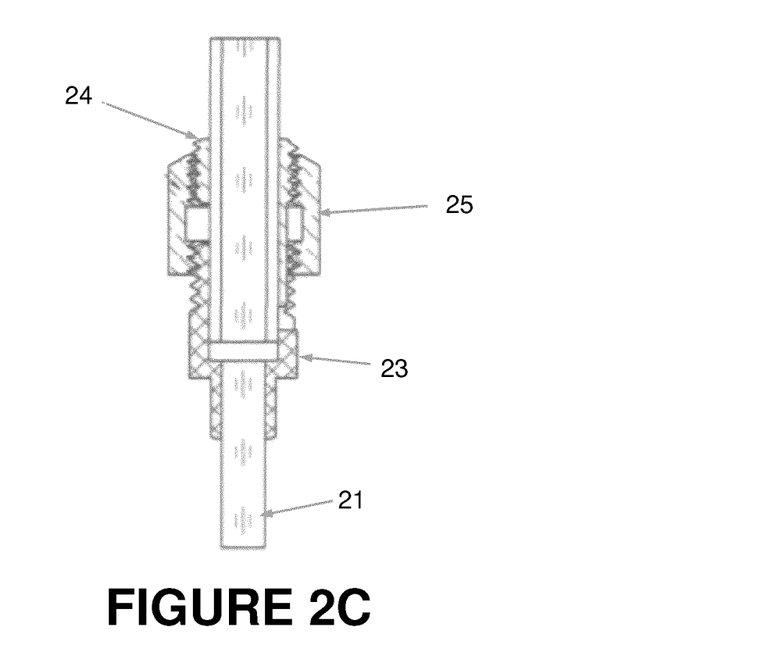
FIG. 2C is a cross-sectional rear view of the connector of FIG. 2A, the direction of the cross section being indicated in FIG. 2B.
Figure 2D:
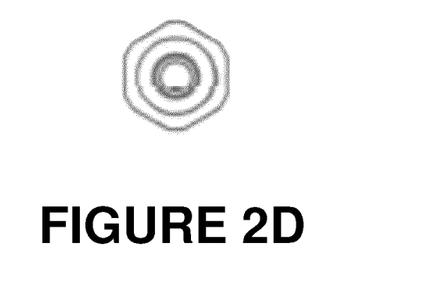
FIG. 2D is a bottom view of the connector of FIG. 2A.

The internal threads of the proximal and distal end of nut 25 are, respectively, in opposite thread directions. That is, one of these internal threads is a left-handed thread, while the other is a right-handed thread. Thus, when the collet 23, nut 25 and ferrule adapter 24 are assembled together, a rotation of the nut in one direction will cause both the collet 23 and the ferrule adapter 24 to be drawn toward each other, while a rotation in the opposite direction will cause them to move further apart. The focusing of the connector can therefore be controlled by a user simply by rotating the nut 25, which may be adjustable by hand, so as to move the lens and fiber relative to each other in an axial direction. When these components are assembled together, tab 27 of the ferrule adapter 24 is located in the slot 26 of the collet 23, thereby maintaining a constant relative rotational orientation of the ferrule adapter and the lens 21. This relative orientation remains regardless of how many times the user disconnects and reconnects the fiber to the lens.

Assembly of the components of the connector shown in FIG. 2A can be done by first attaching the nut 25 to ferrule adapter 24, and then locating them both around the fiber ferrule 22. The nut is advanced on the thread of ferrule adapter 24 until the end of tab 27 arrives at the distal end of the nut 25. The fiber ferrule 22 is then inserted into the collet 23, while aligning the tab 27 and slot 26 and threading together the nut 25 and collet 23 as far as possible. The fiber is then inserted into the ferrule 22 and the lens 21 is inserted into the collet 23, each being advanced as far as possible. At this relative positioning, the fiber is at a distance of about 10-20 microns from the lens. With the assembly at this setting, the lens 21 is glued to the collet 23 and the ferrule adapter 24 is glued to the fiber ferrule 22. Like the embodiment of FIGS. 1A-1E, the embodiment of FIGS. 2A-2D provides miniature repeatable fiber-lens connector that may be used for small animal imaging. The profile of the connector is slimmer, and there are fewer components, but the focus setting is not automatically retained when the fiber ferrule 22 is disconnected from the lens 21 and collet 23. However, the number of turns of the nut 25 may be recorded, or a marking on either or both of the collet 23 and ferrule adapter 27 may be used to identify the proper rotational position of the nut at a desired focus.

The invention claimed is:

1. An optical imaging connector comprising:
   a fiber assembly comprising:
      an optical fiber ferrule in which is located an optical fiber for transporting an optical image;
      a ferrule adapter fixed to the ferrule and having a radial extension with a first coupling portion; and
   a lens assembly comprising:
      a lens with a distal end configured to be fixed adjacent to an imaging target;
      a lens holder in which the lens is mounted with its proximal end adjacent to a ferrule receptacle that receives the ferrule and maintains it in a substantially co-axial relationship with the lens, the lens holder having a radial extension with a second coupling portion that engages the first coupling portion to removably couple the fiber assembly to the lens assembly; and
      a focus adjustment mechanism that is manually adjustable by a user to change a longitudinal position of the second coupling portion relative to the lens holder and thereby change an axial position of the ferrule in the ferrule receptacle.

2. An optical imaging connector according to claim 1 wherein the first and second coupling portions comprise at least one magnetic element that provides a magnetic attraction between the first and second coupling portions.

3. An optical imaging connector according to claim 2 wherein the first and second coupling portions each comprise a magnetic element, and the magnetic elements have a mutual attraction to each other.

4. An optical imaging connector according to claim 1 wherein the radial extension of the lens holder has a threaded aperture and the focus adjustment mechanism comprises a screw having an external thread that meshes with an internal thread of the threaded aperture, and that changes said longitudinal position of the second coupling portion upon rotation of the screw.

5. An optical imaging connector according to claim 4 wherein a head of the screw faces a proximal end of the connector to allow user access from said proximal end of the connector.

6. An optical imaging connector according to claim 1 wherein the ferrule receptacle has an annular inner surface adjacent to the proximal end of the lens that provides a limit on the extent to which the ferrule may be inserted in the lens holder to prevent contact between the ferrule and the lens.

7. An optical imaging connector according to claim 1 wherein the engagement between the first coupling portion and the second coupling portion maintains a constant relative angular orientation between the fiber assembly and the lens assembly.

8. An optical imaging connector according to claim 1 wherein the focus adjustment mechanism changes a longitudinal position of the second coupling portion relative to the first coupling portion along an axis that is parallel to, but radially offset from, a longitudinal axis of the ferrule and lens holder.

9. An optical imaging connector according to claim 1 wherein manual adjustment of the focus adjustment mechanism is accessible to the user from a proximal end of the connector.

10. An optical imaging connector comprising:
    an optical fiber ferrule in which is located an optical fiber for transporting an optical image;
    a ferrule adapter fixed to the ferrule and having an external screw thread and an axially-extending detent on a distal side of the adapter;
    a lens with a distal end configured to be fixed adjacent to an imaging target;
    a lens holder in which the lens is mounted with its proximal end adjacent to a ferrule receptacle that receives the ferrule and maintains it in a substantially co-axial relationship with the lens, the lens holder having an external screw thread and receiving the detent when the ferrule adapter and the lens holder are axially adjacent to each other so as to prevent a relative rotation therebetween; and
    a focus adjustment mechanism with an internal screw thread that engages both the screw thread of the ferrule adapter and the screw thread of the lens holder, and that is manually rotatable by a user to change a relative longitudinal position between the ferrule adapter and the lens holder and thereby change an axial position of the ferrule in the ferrule receptacle.

11. An optical imaging connector according to claim 10 wherein the detent comprises a tab that extends from the ferrule adapter and wherein the lens holder comprises an axial slot that receives the tab.

12. An optical imaging connector according to claim 10 wherein the focus adjustment mechanism comprises a nut with screw threads having different thread directions at either of two openings of the nut.

13. An optical imaging connector according claim 10 wherein the focus adjustment mechanism maintains the ferrule adapter and the lens holder in a substantially coaxial position relative to each other.

14. An optical imaging connector according to claim 13 wherein rotation of the focus adjustment mechanism to an extreme provides disengagement of the internal screw thread with the screw threads of the ferrule adapter and the lens holder, and allows detachment of the ferrule from the lens holder.

* * * * *